(12) United States Patent
Kubota

(10) Patent No.: US 9,746,436 B2
(45) Date of Patent: Aug. 29, 2017

(54) DETECTING DEVICE, DETECTING CIRCUIT, SENSOR MODULE AND IMAGE FORMING DEVICE

(71) Applicant: Shinichi Kubota, Osaka (JP)

(72) Inventor: Shinichi Kubota, Osaka (JP)

(73) Assignee: RICOH COMPANY, LTD., Tokyo (JP)

( * ) Notice: Subject to any disclaimer, the term of this patent is extended or adjusted under 35 U.S.C. 154(b) by 238 days.

(21) Appl. No.: 14/608,596

(22) Filed: Jan. 29, 2015

(65) Prior Publication Data

US 2015/0253270 A1 Sep. 10, 2015

(30) Foreign Application Priority Data

Mar. 7, 2014 (JP) ................. 2014-044848

(51) Int. Cl.
*G01N 27/04* (2006.01)

(52) U.S. Cl.
CPC ................. *G01N 27/048* (2013.01)

(58) Field of Classification Search
CPC .................................................. G01N 27/048
USPC ........................................................ 324/705
See application file for complete search history.

(56) References Cited

U.S. PATENT DOCUMENTS

| | | | |
|---|---|---|---|
| 4,347,479 A * | 8/1982 | Cullet | G01R 31/2884 257/E21.53 |
| 5,517,151 A | 5/1996 | Kubota | |
| 5,551,283 A | 9/1996 | Manaka et al. | |
| 5,815,025 A | 9/1998 | Kubota | |
| 7,336,687 B2 | 2/2008 | Kubota | |
| 7,369,590 B2 | 5/2008 | Kubota | |
| 7,599,416 B2 | 10/2009 | Kubota | |
| 7,609,735 B2 | 10/2009 | Kubota | |
| 8,147,131 B2 | 4/2012 | Goto et al. | |
| 8,729,971 B2 | 5/2014 | Kubota | |
| 2001/0040241 A1 * | 11/2001 | Nagano | G01D 3/02 257/159 |
| 2004/0069061 A1 * | 4/2004 | Watanabe | G01F 1/6842 73/204.26 |

(Continued)

FOREIGN PATENT DOCUMENTS

| | | |
|---|---|---|
| JP | 2889909 | 5/1999 |
| JP | 3124609 | 1/2001 |

(Continued)

*Primary Examiner* — Patrick Assouad
*Assistant Examiner* — Khristopher Yodichkas
(74) *Attorney, Agent, or Firm* — Cooper & Dunham LLP

(57) ABSTRACT

A detecting device includes a substrate having a cavity portion in the surface thereof; a thin-film layer formed over the cavity portion; an on-thin-film layer pattern formed on the thin-film layer; an on-substrate pattern formed on the substrate; and a first terminal, a second terminal, a third terminal, and a fourth terminal. A resistance between the first terminal and the second terminal includes a resistance of the on-thin-film layer pattern, a resistance between the third terminal and the fourth terminal includes the resistance of the on-thin-film layer pattern and a resistance of the on-substrate pattern, and the resistance between the first terminal and the second terminal is less than the resistance between the third terminal and the fourth terminal.

15 Claims, 11 Drawing Sheets

(56) References Cited

U.S. PATENT DOCUMENTS

| | | | |
|---|---|---|---|
| 2007/0113644 A1* | 5/2007 | Manaka | G01F 1/684 |
| | | | 73/204.26 |
| 2012/0013383 A1 | 1/2012 | Negoro et al. | |
| 2013/0192388 A1* | 8/2013 | Kono | G01F 1/6845 |
| | | | 73/861.47 |
| 2014/0079458 A1 | 3/2014 | Seto et al. | |

FOREIGN PATENT DOCUMENTS

| | | |
|---|---|---|
| JP | 3460749 | 10/2003 |
| JP | 2013-054948 | 3/2013 |

* cited by examiner

DETECTING DEVICE, DETECTING CIRCUIT, SENSOR MODULE AND IMAGE FORMING DEVICE

BACKGROUND OF THE INVENTION

1. Field of the Invention

The present technology relates to a detecting device, a detecting circuit, a sensor module and an image forming device.

2. Description of the Related Art

A detecting device, having a micro bridge structure and availing of thermal conductivity, is widely known as a detecting device for detecting a status of the atmosphere such as humidity.

As for a specific structure of the detecting device, in Japanese Patent Gazette No. 3124609, for example, a disclosed structure includes a heating resistor (heating element pattern) formed on a cavity portion in a substrate through an insulator thin-film having a bridge supported portion.

The detecting device, having such structure, detects variances of voltage indicating variances of thermal conductivity, responsive to a status of the atmosphere in the vicinity of the heating element pattern, when the heating element is heated to high temperature, thereby generating a signal relating to the status of the atmosphere. Here, a signal relating to the status of the atmosphere includes a temperature component as well as a humidity component. Thus, a signal, which relates to only temperature, is required to be generated in order to distinguish the temperature component from the humidity component.

Therefore, as disclosed in Japanese Patent Gazette No. 3124609, a signal relating to temperature has been generated by detecting variances of resistance indicating variances of voltage, responsive to variances of temperature of the heating element pattern. The heating element is heated to room temperature. Then, the signal relating to the status of the atmosphere is corrected based on the signal relating to temperature, and thereby a desired signal relating to the status of the atmosphere (such as humidity) is generated.

However, in a case where the signal relating to temperature is generated using the heating element pattern in the detecting device as disclosed in Japanese Patent Gazette No. 3124609, current supplied to the heating element has to be kept small so that the heating element does not heat itself. Then, the variance of voltage of the heating element pattern becomes small making it difficult to generate the signal relating to temperature with high sensitivity, and to generate the signal relating to the status of the atmosphere, which is corrected based on the signal relating to temperature, with high precision.

RELATED ART DOCUMENT

Patent Document

[Patent Document 1]: Japanese Patent Gazette No. 3124609

SUMMARY OF THE INVENTION

An object of disclosure of the present technology is to generate the signal relating to the status of the atmosphere with high precision.

The following configuration is adopted to achieve the aforementioned object.

In one aspect of an embodiment, a detecting device includes a substrate having a cavity portion in the surface thereof; a thin-film layer formed over the cavity portion, an on-thin-film layer pattern formed on the thin-film layer; an on-substrate pattern formed on the substrate; and a first terminal, a second terminal, a third terminal, and a fourth terminal. A resistance between the first terminal and the second terminal includes a resistance of the on-thin-film layer pattern, a resistance between the third terminal and the fourth terminal includes the resistance of the on-thin-film layer pattern and a resistance of the on-substrate pattern, and the resistance between the first terminal and the second terminal is less than the resistance between the third terminal and the fourth terminal.

Other objects, features and advantages of the present invention will become more apparent from the following detailed description when read in conjunction with the accompanying drawings.

DETAILED DESCRIPTION OF THE PREFERRED EMBODIMENTS

First Embodiment

Herein below, an example of a configuration of a detecting device 100a of the first embodiment will be described.

The detecting device 100a of the present embodiment is characterized by a substrate having a cavity portion on the surface thereof; a thin-film layer formed over the cavity portion; an on-thin-film layer pattern formed on the thin-film layer; an on-substrate pattern formed on the substrate; and a first terminal, a second terminal, a third terminal, and a fourth terminal. A resistance between the first terminal and the second terminal includes a resistance of the on-thin-film layer pattern, a resistance between the third terminal and the fourth terminal includes the resistance of the on-thin-film layer pattern and a resistance of the on-substrate pattern, and the resistance between the first terminal and the second terminal is less than the resistance between the third terminal and the fourth terminal.

In the following, a heating element pattern is described as an example of an on-thin-film layer pattern, while a resistor pattern is described as an example of an on-substrate pattern.

Figure 1A:
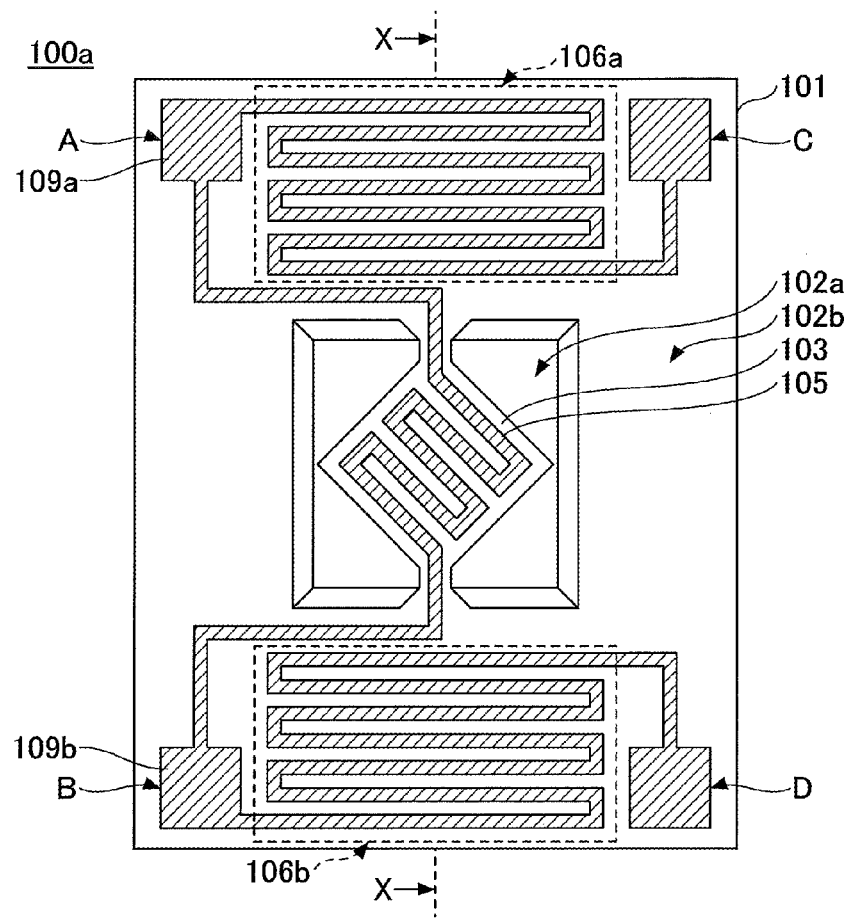
FIG. 1A is a plan view of the detecting device of the first embodiment.
Figure 1B:
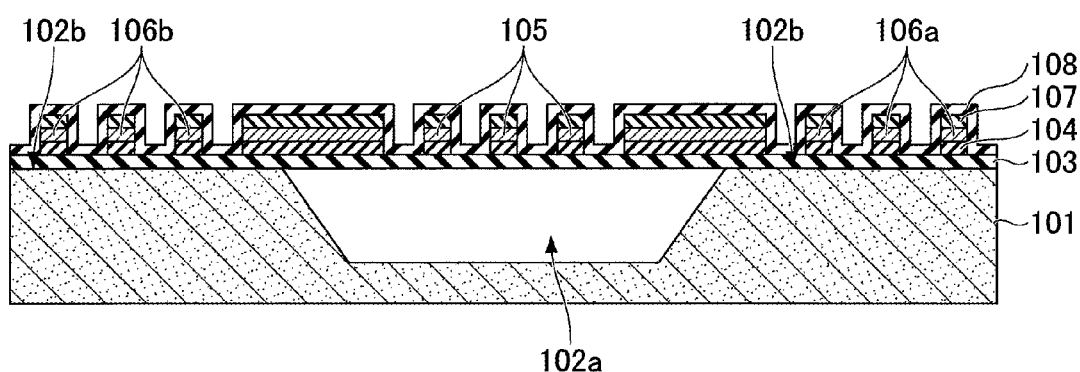
FIG. 1B is a cross-sectional view taken in X-X of FIG. 1A.

In FIG. 1A and FIG. 1B, a schematic diagram of an example of the detecting device 100a is illustrated. FIG. 1A is a plan view of the detecting device 100a. FIG. 1B is a cross-sectional view taken in X-X of FIG. 1.

As described in FIG. 1A and FIG. 1B, the detecting device 100a of the first embodiment includes a substrate 101 including a cavity portion 102a on which a cavity is formed, and a non-cavity portion 102b on which no cavity is formed, a lower insulating layer 103 which is a bridge-supported or one-end supported thin-film layer over the cavity portion 102a, a heating element pattern 105 which is formed on a first adhesive layer 104 on the lower insulating layer 103, and resistor patterns 106a and 106b which are formed on the first adhesive layer 104 on the lower insulating layer 103 in the non-cavity portion 102b.

Also, a second adhesive layer 107 and an upper insulating layer 108 are formed on the heating element pattern 105 and the resistor patterns 106a and 106b.

One end of the heating element pattern 105 is connected with one end of the resistor pattern 106a to form a connecting portion 109a. The other end of the heating element pattern 105 is connected with one end of the resistor pattern 106b to form a connecting portion 109b.

A terminal A, as a first terminal, is formed with the connecting portion 109a, where the heating element pattern 105 and the resistor pattern 106a are connected with each other, and a terminal B, as a second terminal, is formed with the connecting portion 109b, where the heating element pattern 105 and the resistor pattern 106b are connected. Further, a terminal C, as a third terminal, is formed on the other end of the resistor pattern 106a, while a terminal D, as a fourth terminal, is formed on the other end of the resistor pattern 106b.

The terminals A, B, C and D are, for example, used as electrode pads for connecting with external circuits. That is, through the terminals A, B, C and D connected with leads (not shown), external circuits are connected. Thus, current is supplied to the heating element pattern 105 and the resistor patterns 106a and 106b; then, signals of voltage, current or the like between desired terminals can be generated.

When current is supplied to the heating element pattern 105 and the resistor patterns 106a and 106b, the heating element pattern 105 generates a signal relating to a status (characteristic) of the atmosphere and the resistor patterns 106a and 106b and the heating element pattern 105 generate a signal relating to temperature.

As for the status of the atmosphere, humidity, atmospheric pressure, gas concentration or the like are exemplified. In a case where the status of the atmosphere is humidity, the detecting device 100a serves as a humidity sensor. Also, in a case where the status of the atmosphere is atmospheric pressure, the detecting device 100a serves as an atmospheric pressure sensor. Further, in a case where the status of the atmosphere is gas concentration, the detecting device 100a serves as a gas sensor.

Here, the detecting device is controlled, by supplying current to the detecting device 100a, to heat the heating element pattern 105 so as to constantly keep a temperature of 300° C. In this case, the signal relating to the status of the atmosphere is generated by detecting voltage variances between the terminals A and B of the heating element pattern 105 indicating thermal conductivity variances responsive to a status of the atmosphere in the vicinity of the heating element pattern 105.

Meanwhile, since the signal relating to the status of the atmosphere includes a temperature component, the signal needs to be corrected by eliminating a signal relating to temperature from the signal relating to the status of the atmosphere; therefore the signal relating to temperature needs to be generated.

The signal relating to temperature can be generated by detecting voltage variances between the terminals C and D, indicating resistance variances of portions including the heating element 105 and the resistor patterns 106a and 106b responsive to temperature variances, while a small current is supplied to the detecting device 100a so that the detecting device 100a is kept around room temperature.

Then, a desired signal relating to the status of the atmosphere is generated by correcting the signal relating to the status of the atmosphere based on the signal relating to temperature.

In this case, since the resistance between the terminals C and D becomes a value which is the sum of values of the resistance between terminals A and B and the resistance of resistor patterns 106a and 106b, the resistance between the terminals C and D becomes larger than the resistance between the terminals A and B. Therefore, even in a case where a small current is supplied to the detecting device 100a, large variances of voltage indicating variances of resistance responsive to temperature can be detected, compared with a configuration in which only the heating element 105 is formed between terminals.

As a consequence, the signal relating to the status of the atmosphere can be corrected based on the signal relating to temperature with high sensitivity, and thereby a signal relating to the status of the atmosphere can be generated with high precision. Further, measures against noise, disposing an amplifier circuit with a large amplification factor in downstream of the detecting device 100a, and the like are not required.

The resistor patterns 106a and 106b are formed on the non-cavity portion 102b. Therefore, heat generated by the resistor patterns 106a and 106b is transferred through the substrate 101. That is, the heat generated by the resistor patterns 106a and 106b is easily conducted compared with heat generated by the heating element pattern, which is formed on a thin-film layer being bridge-supported or one-end-supported over the cavity portion 102a.

Therefore, the resistance of the resistor patterns 106a and 106b can be set to a larger value than that of heating element pattern 105, and the voltage detected between the terminals C and D becomes large. Thus, the variances of resistance responsive to temperature can be detected as the variances of voltage with high sensitivity, compared with a case where the small current is supplied only to the resistance of the heating element pattern 105.

As described above, according to the detecting device 100a of the first embodiment, the signal relating to the atmosphere can be generated with high precision.

Additionally, although the first embodiment is directed to a configuration of the detecting device 100a in which one heating element pattern 105 and two resistor patterns 106a and 106b are included, this is not a limited example. That is, the detecting device may only include one or more heating element patterns 105 and one or more resistor patterns. For example, the detecting device may be configured to include one heating element 105 and one resistor pattern 106a.

In the following, an example for a method of manufacturing the detecting device 100a will be described.

Figure 2:
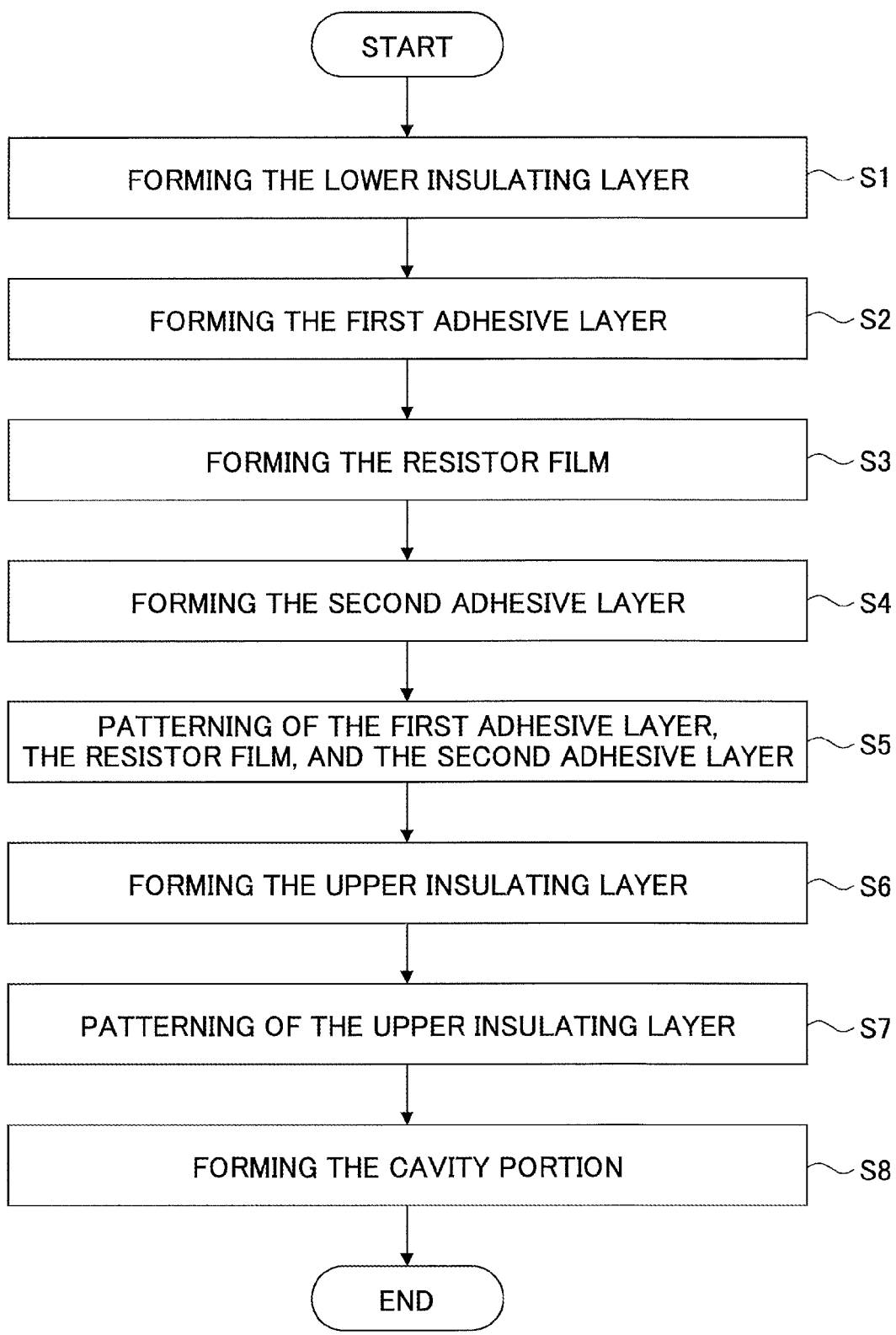
FIG. 2 is a flowchart illustrating a method of manufacturing the detecting device of the first embodiment.

FIG. 2 is a flowchart illustrating an example of a method of manufacturing the detecting device 100a of the first embodiment. Herein below, steps of the flowchart will be described with respect to FIG. 2.

In step S1, for example, the lower insulating layer 103 made of silicon dioxide (SiO2), silicon nitride (Si3N4) or the like is formed on the substrate 101 made of silicon, by a CVD (Chemical Vapor Deposition) process, a sputtering process, or the like.

In step S2, for example, the first adhesive layer 104 made of insulating material such as tantalum pentaoxide (Ta2O5) is formed on the lower insulating layer 103, by a CVD process, a sputtering process, or the like.

In step S3, a resistor film for forming the heating element pattern 105, the resistor patterns 106a and 106b, and the terminals A, B, C and D is formed on the first adhesive layer 104, by a vapor deposition process, a CVD process, a sputtering process, or the like. As for the resistor film, platinum (Pt), gold (Au), nickel chrome (NiCr), or tungsten (W) is exemplified. Especially, Pt has stable physical properties, and has a larger temperature coefficient of the resistance than that of other metals. Further, linearity of the temperature coefficient is high in a wide range of temperatures. Therefore, Pt is a suitable material for both of the heating material pattern 105 and the temperature detecting resistor (resistor patterns 106a and 106b, in this embodiment).

In step S4, the second adhesive layer 107, which is made of insulating materials such as Ta2O5, is formed on the resistor film by a CVD process, a sputtering process, or the like.

In step S5, the first adhesive layer 104, the resistor film and the second adhesive layer 107 are worked into a desired shape, for example, by photolithography. That is, the heating element pattern 105, the resistor patterns 106a and 106b, and the terminals A, B, C and D are formed.

In step S6, to secure the insulation between the terminals, the upper insulating layer 108 made of SiO2, SiN4, etc., is formed on the second adhesive layer 107 by a CVD process, a sputtering process, or the like.

In step S7, the upper insulating layer 108 is worked into a desired shape, for example, by photolithography.

In step S8, the cavity portion 102 is formed by performing an anisotropic etching process on the substrate 101 with etching liquid such as tetraethylammonium hydroxide (TMAH), potassium hydroxide (KOH), or the like.

Through the steps S1-S8 described above, the detecting device 100a of the first embodiment is manufactured.

Figure 3:
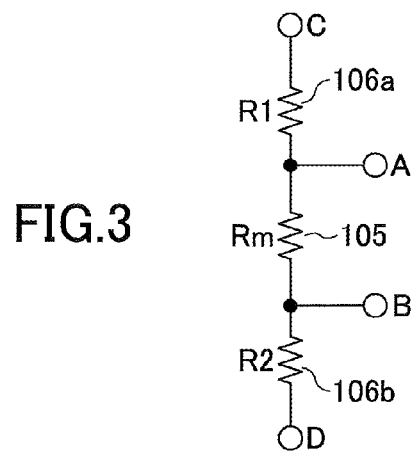
FIG. 3 is an equivalent circuit diagram of the detecting device shown in FIG. 1.

FIG. 3 is an equivalent circuit diagram of the detecting device 100a shown in FIG. 1. In FIG. 3, "Rm" shows a resistance of the heating element pattern 105, "R1" shows a resistance of the resistor pattern 106a, "R2" shows a resistance of the resistor pattern 106b.

In FIG. 3, the resistance Rm of the heating element 105, at a temperature of 20° C., is 140Ω, while a sum of the resistance of the resistor patterns 106a and 106b (R1+R2), at a temperature of 20° C., is 1260Ω. In this case, a combination of terminals A and B serves as a sensor (of 140Ω) for detecting humidity, while a combination of the terminals C and D serves as a sensor (of 1400Ω) for detecting temperature.

When, for example, 100 μA current flows through 1400Ω resistance between the terminals C and D, a voltage generated between the terminals C and B becomes 140 mV. This voltage is ten times larger than a voltage of a case where the resistor patterns 106a and 106b are not formed (i.e. resistance of 140Ω). That is, detection sensitivity of the detecting device 100a can be ten times larger by forming the resistor patterns 106a and 106b.

In this case, power consumption between the terminals C and D becomes 14 μW which is ten times larger than power consumption (1.4 μW) of a case where the resistor patterns 106a and 106b are not formed. However, temperature rarely rises and heating is unlikely to be caused since the resistor patterns 106a and 106b are formed on the substrate 101 which has high thermal conductivity.

In the following, detecting circuits using the detecting device 100a will be described with respect to FIG. 4-FIG. 6.

Figure 4:
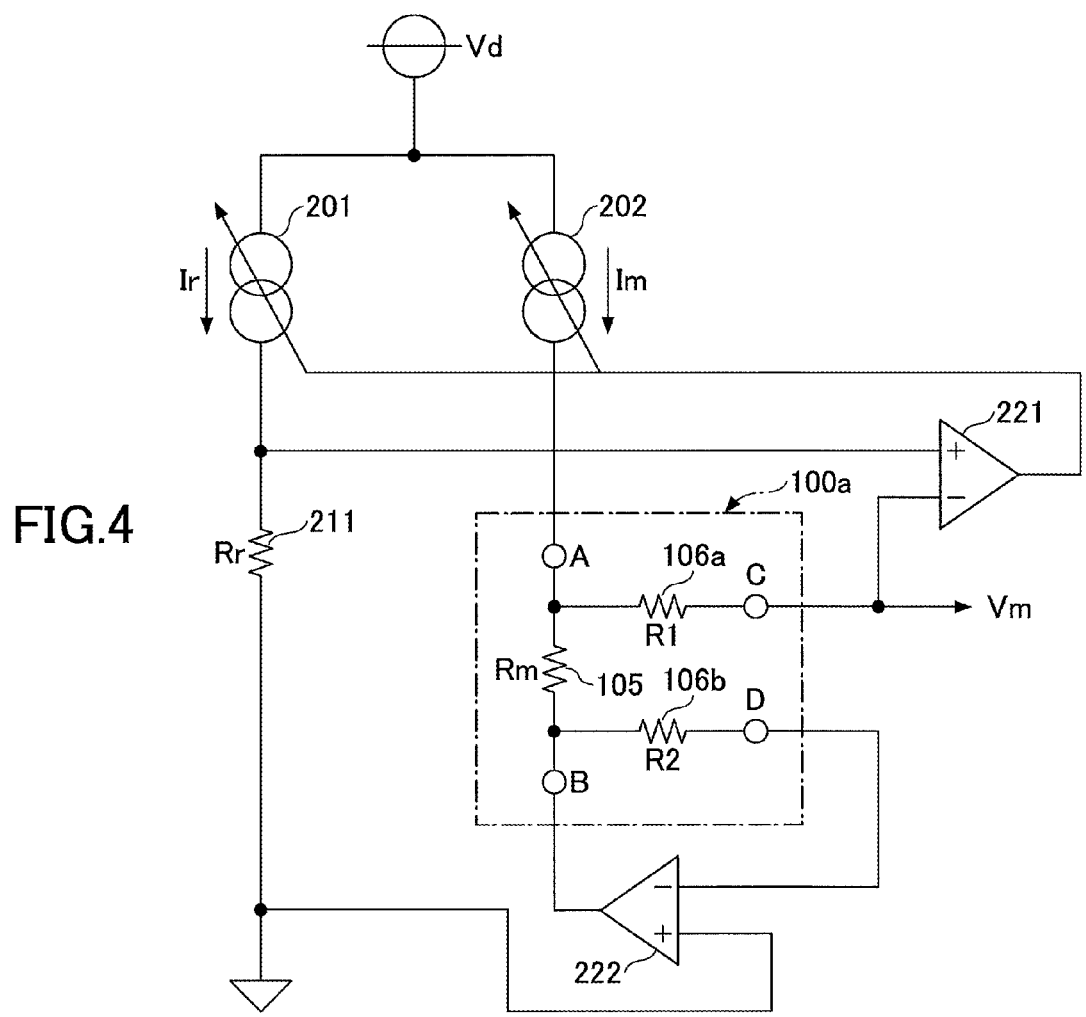
FIG. 4 is a circuit diagram illustrating an example of a detecting circuit using the detecting device.

FIG. 4 is a circuit diagram illustrating an example of a detecting circuit using the detecting device 100a. In FIG. 4, "Vd" shows a source voltage.

The detecting circuit shown in FIG. 4 is an example case where the detecting device 100a is connected with an external circuit, the detecting circuit including detecting device 100a, a first constant current source 201 which is a variable type constant current source, a second constant current source 202 which is a variable type constant current source, a reference resistor 211 and operational amplifiers 221 and 222, wherein the detecting circuit detects a status of the atmosphere in the vicinity of the heating pattern 105.

In the detecting circuit shown in FIG. 4, a value of an output current Ir supplied by the first constant current source 201 is controlled by the operating amplifier 221 to be equal to a value of output current Im supplied by the second constant current source 202. Specifically, the operational amplifier 221 compares a voltage generated by the reference resistor 211 and a voltage generated by the detecting device 100a, and thereby controls the first constant current source 201 and the second constant current source 202 in combination with each other so that the generated voltages become equal.

Here, the embodiment is described, in a case where the heating pattern 105 made of Pt, having the resistance Rm of 143.0Ω at a temperature of 20° C., is heated so as to constantly keep a temperature of 300° C. In this case, the resistance of Pt becomes 299.2Ω at a temperature of 300° C. since the temperature coefficient of the resistance of Pt is 3900 ppm/° C.

The operational amplifier 221 controls currents Ir and Im, respectively supplied by the first constant current source 201 and the second constant current source 202, so that the resistance of Pt becomes equal to a resistance Rr of the reference resistor, the resistance Rr of the reference resistor being the same as that of the resistance (299.2Ω) of Pt at a temperature of 300° C.

That is, the detecting circuit is, for example, configured to control to constantly keep a high temperature of 300° C. by supplying output current Im to the detecting device 100a to heat the Pt. Then, the detecting circuit detects variances of thermal conductivity responsive to a status of the atmosphere in the vicinity of the heating element pattern, as variances of voltage Vm expressed by formula (1), thereby generating a signal relating to the status of the atmosphere.

$$Vm = Im \times Rm \tag{1}$$

Here, input impedances of the operational amplifier 221 and operational amplifier 222 are preferably large enough. Due to that, current rarely flows in the resistor pattern 106a and the resistor pattern 106b, so that an electric potential at the terminal A is almost equal to that at the terminal C and an electric potential at the terminal B is almost equal to that at the terminal D. That is, the resistance R1 of the resistor pattern 106a and the resistance R2 of the resistor pattern 106b can be disregarded in the calculation. As a result, formula (1) is established and a signal relating to the status of the atmosphere can be generated with high precision.

As described above, the resistance Rm of the heating element pattern 105 is controlled to become equal to the resistance Rr of the reference resistor 211, regardless of thermal conductivity of gas in the vicinity of the detecting circuit. Thus, herein below, the detecting circuit shown in FIG. 4 may be referred as a constant resistance circuit 200a.

Additionally, a relative large current of 6 mA, for example, is required in order to heat the heating element 105 to a high temperature of 300° C. In this case, the output voltage Vm becomes 1.80 V calculated by formula (1), which is a voltage high enough to be handled by a microcomputer, etc., without being amplified.

By the way, as for the first constant current source 201 and the second constant current source 202 which are controlled in combination with each other in the example described above, although current Im, which is not small, flown in heating element pattern 105 also flows in the first constant current source 201 and the second constant current source 202, this is not a limiting example. For example, current consumption of the constant current source 201, which is the constant current source in the reference resistor 211 side, can be reduced by setting a certain current ratio between the first constant current source 201 and the second constant current source 202.

Specifically, for example, the current ratio between the first constant current source 201 and the second constant current source 202 may be set as 1:10. In this case, current flowing in the reference resistor 211 (resistance Rr) becomes $\frac{1}{10}$, thereby the resistance of the reference resistor 211 needs to be changed to 10 times larger. It is meaningful to reduce the current as described above since the reference resistor 211 does not need to be heated.

Figure 5:
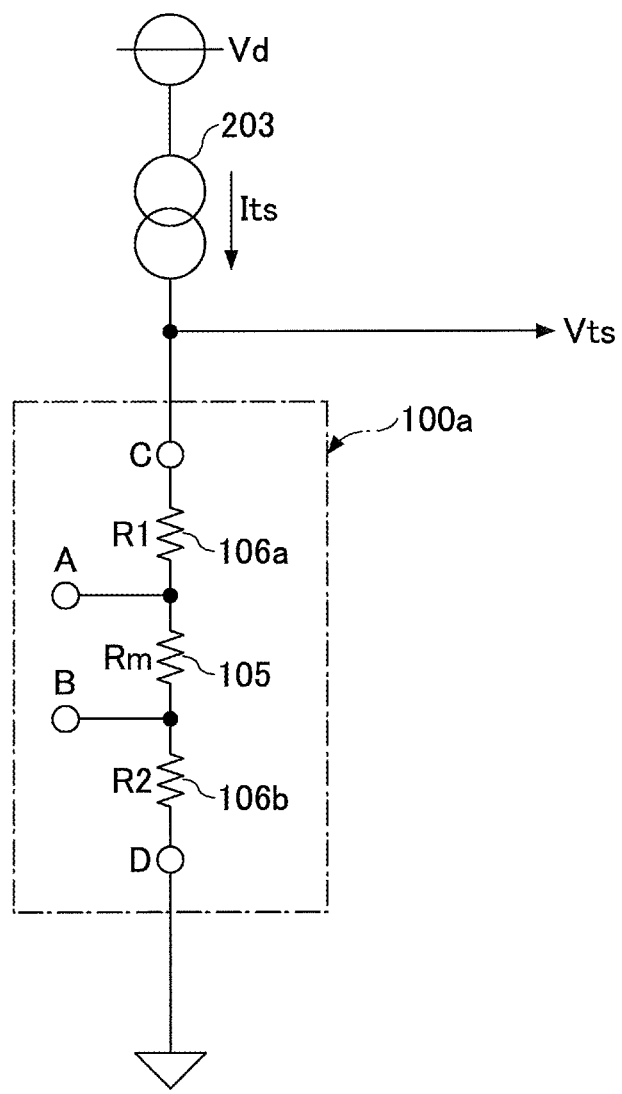
FIG. 5 is a circuit diagram illustrating another example of a detecting circuit using the detecting device.

FIG. 5 is a circuit diagram illustrating another example of a detecting circuit using the detecting device 100a.

The detecting circuit shown in FIG. 5 is an example case where the detecting device 100a is connected with an external circuit, the detecting circuit including detecting device 100a and a third constant current source 203, wherein the detecting circuit detects temperature in the vicinity of the resistor patterns 106a and 106b, and the heating pattern 105.

In the detecting circuit shown in FIG. 5, a signal relating to temperature in the vicinity of the resistor patterns 106a and 106b and the heating element pattern 105 is generated by measuring a voltage Vts between the terminals C and D which is generated by current Its supplied by the third constant current source 203. Here, the voltage Vts between the terminals C and D is expressed by formula (2).

$$Vts=Its\times(R1+Rm+R2) \quad (2)$$

Additionally, the detecting circuit is controlled to supply constant current to the detecting device 100a by the third constant current source 203. Thus, herein below, the detecting circuit shown in FIG. 5 may be referred as a constant current circuit 300a.

Figure 6:
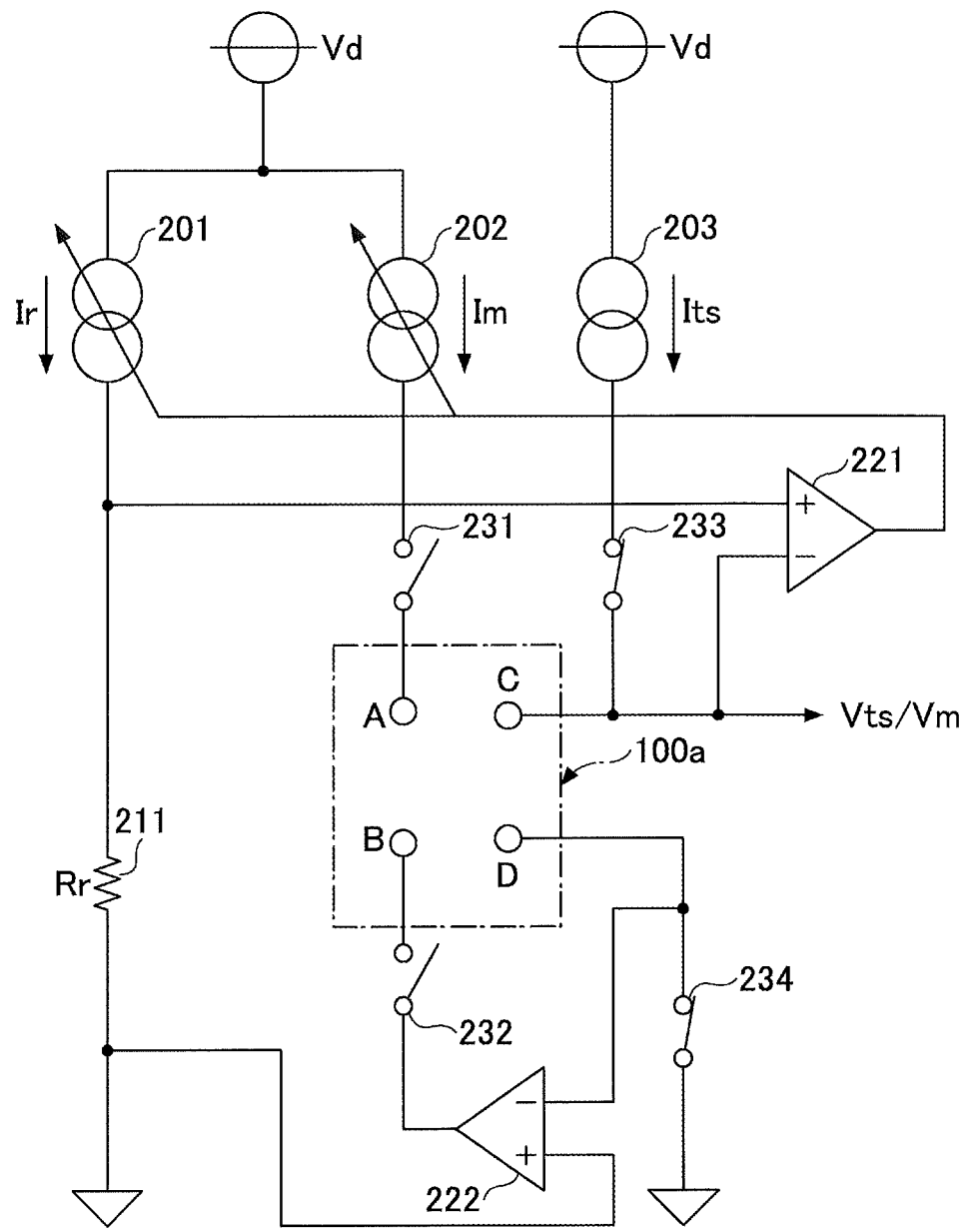
FIG. 6 is a circuit diagram illustrating still another example of a detecting circuit using the detecting device.

FIG. 6 is a circuit diagram for illustrating still another example of a detecting circuit using the detecting device 100a.

The detecting circuit shown in FIG. 6 is an example case where the detecting device 100a is connected with an external circuit, the detecting circuit including the detecting device 100a, the first constant current source 201, the second constant current source 202, the third constant current source 203, the reference resistor 211, the operational amplifiers 221 and 222, and switches 231, 232, 233 and 234 as a changeover means. The detecting circuit is a circuit for generating a signal relating to the status of the atmosphere in the vicinity of the heating element pattern 105 and for generating a signal relating to temperature in the vicinity of the resistor patterns 106a and 106b and the heating element pattern 105, through on-off operations of the switches 231, 232, 233 and 234.

As shown in FIG. 6, the detecting circuit is configured to be capable of changing over between generating the signal relating to the status of the atmosphere and generating the signal relating to temperature, through on-off operations of the switches 231, 232, 233 and 234.

That is, when the switches 231 and 232 are switched on and the switches 233 and 234 are switched off, the detecting circuit serves, similarly to the circuit shown in FIG. 4, as a constant resistance circuit 200a (a first circuit) to generate the signal relating to the status of the atmosphere in the vicinity of the heating element pattern 105. Meanwhile, when the switches 231 and 232 are switched off and the switches 233 and 234 are switched on, the detecting circuit serves, similarly to the circuit shown in FIG. 5, as a constant current circuit 300a (a second circuit) to generate the signal relating to the temperature in the vicinity of the resistor patterns 106a and 106b and the heating element pattern 105.

According to the detecting circuit shown in FIG. 6, the signal relating to the status of the atmosphere and the signal relating to temperature can be detected using one detecting device 100a. Therefore, the number of parts in the detecting circuit can be reduced.

In the following, a sensor module, including the constant resistance circuit 200a shown in FIG. 4 and the constant current circuit 300a shown in FIG. 5, will be described with respect to FIG. 7.

Figure 7:
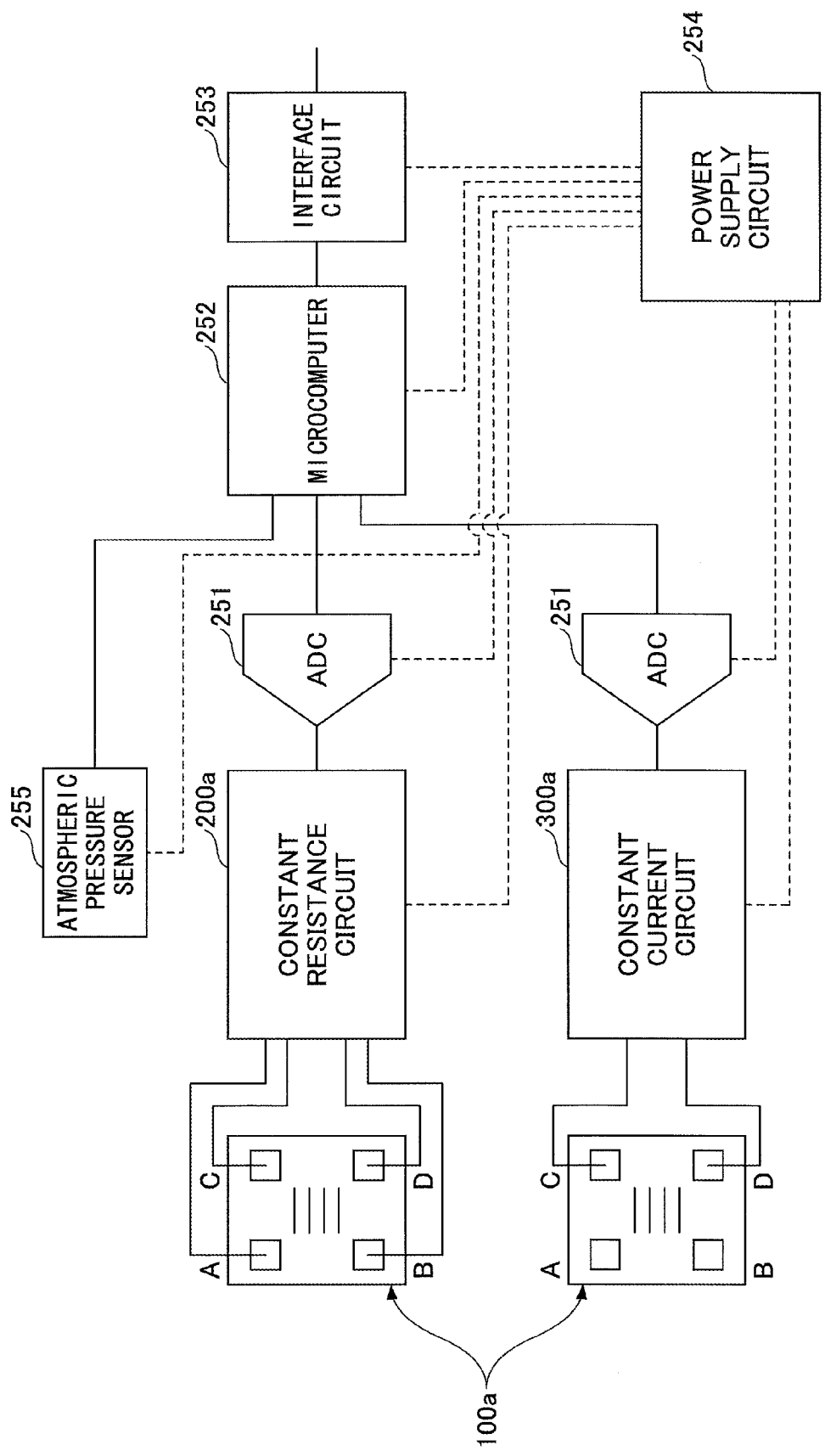
FIG. 7 is a block diagram of an example of a sensor module using a constant resistance circuit and a constant current circuit.

FIG. 7 is a block diagram of an example of a sensor module using the constant resistance circuit 200a and the constant current circuit 300a. In FIG. 7, solid lines show signal lines, while dotted lines show power supply lines.

The sensor module shown in FIG. 7 includes the constant resistance circuit 200a, the constant current circuit 300a, two Analog-to-Digital converters (ADC) 251, a microcomputer 252 and an interface circuit 253 as a control unit. The sensor module is a module which is operated by supplying power from a power supply circuit 254 to respective circuits.

As shown in FIG. 7, voltage signals (analog signal) respectively detected by the constant resistance circuit 200a and the constant current circuit 300a are converted into digital signals by the ADCs 251. Further, the digital signals are processed in the microcomputer 252 thereby outputting a signal relating to the status of the atmosphere, corrected based on temperature, through the interface circuit 253.

At this time, the signal relating to the status of the atmosphere has been corrected based on temperature. Therefore, the signal relating to the status of the atmosphere can be generated with high precision.

Further, a signal relating to temperature may be output through the interface circuit 253 as well as the signal relating to the status of the atmosphere. Thus, two signals relating to the status of the atmosphere and relating to temperature can be generated by one sensor module.

Preferably, the sensor module includes an atmospheric pressure sensor 255 connected with the microcomputer 252. In this case, the microcomputer 252 can correct the signal relating to the status of the atmosphere detected by the constant resistance circuit 200a based on the atmospheric pressure detected by the atmospheric pressure sensor, thereby generating the signal relating to the status of the atmosphere with very high precision.

Additionally, in FIG. 7, although a configuration in which ADCs 251 are disposed for both of the constant resistance circuit 200a and the constant current circuit 300a is described, this is not a limiting example. For example, the voltage signals output from the constant resistance circuit 200a and constant current circuit 300a may be converted by one ADC 251 performing time division processing.

Further, in FIG. 7, although a configuration is disclosed in which the ADCs 251 and microcomputer 252 are separately disposed, this is not a limiting example. The ADCs 251 may be integrated with the microcomputer 252.

Also, preferably, the microcomputer 252 has a function to perform a correction operation for correcting variations in characteristics of detecting devices 100a, wherein the detecting devices 100a are used as sensor elements. In this case, an external circuit for correcting the variations in characteristics of the detecting devices 100a is not required.

Further, the sensor module may be applied to, for example, an image forming device such as a copy machine, a fax machine, a printer, a multifunction machine, and the like.

The image forming device including the sensor module can be controlled to operate with very high precision since the status of the atmosphere such as humidity, etc., and temperature in the image forming device can be more precisely detected.

As described above, according to the detecting device 100a, the detecting circuit, the sensor module and the image forming device of the first embodiment, the signal relating to temperature can be generated with high sensitivity. Also, the signal relating to the status of the atmosphere can be generated with high precision since a signal relating to the status of the atmosphere can be corrected based on the signal relating to temperature with high sensitivity. As a consequence, measures against noise, disposing an amplifier circuit with a large amplification factor downstream of the detecting device 100a, and the like are not required.

Second Embodiment

In the following, an example of a detecting device 100b of a second embodiment will be described with reference to FIG. 8 and FIG. 9. Additionally, in the second embodiment, an identical reference numeral will be applied to elements or the like that have substantially the same functions and configurations as those of in the first embodiment, and descriptions thereof will be omitted.

Figure 8:
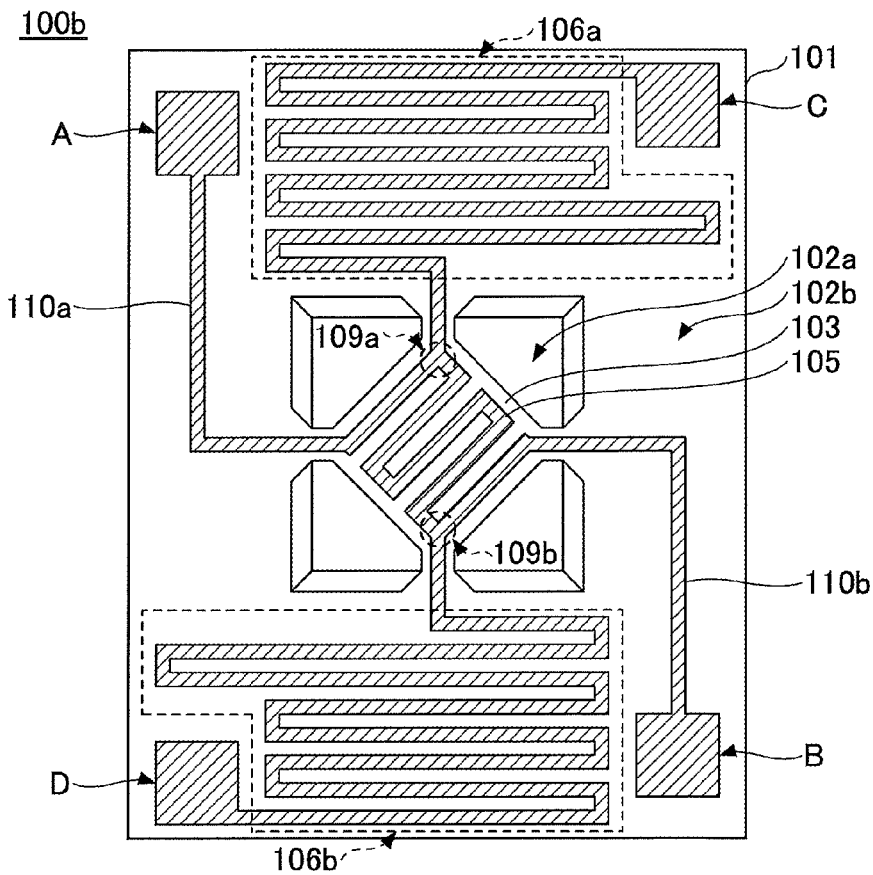
FIG. 8 is a schematic diagram of an example of the detecting device.
Figure 9:
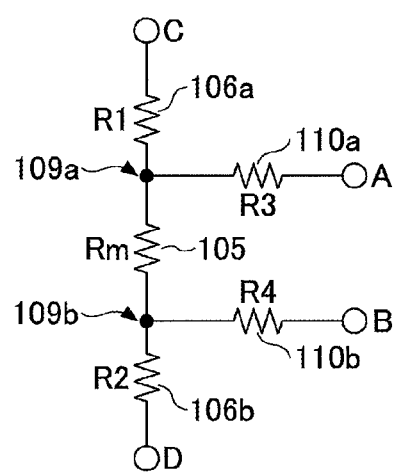
FIG. 9 is an equivalent circuit diagram of the detecting device shown in FIG. 8.

FIG. 8 is a schematic diagram of an example of the detecting device 100b. FIG. 9 is an equivalent circuit diagram of the detecting device 100b shown in FIG. 8. In FIG. 9, "Rm" shows a resistance of the heating element pattern 105, "R1" shows a resistance of the resistor pattern 106a, "R2" shows a resistance of the resistor pattern 106b, "R3" shows a parasitic resistance of a line 110a disposed between the connecting portion 109a and the terminal A, and "R4" shows a parasitic resistance of a line 110b disposed between the connecting portion 109b and the terminal B.

As shown in FIG. 8, in the detecting device 100b of the second embodiment, the connecting portions 109a and 109b are formed on the lower insulating layer 103 that is bridge-supported or one-end-supported over the cavity portion 102a, which is different from the first embodiment.

In the detecting device 100b shown in FIG. 8, by supplying current between the terminal A and B with the constant resistance circuit, a signal relating to humidity is generated based on a voltage between the connecting portion 109a and the connecting portion 109b, i.e. a voltage between the terminals C and D which is equivalent to a voltage generated by the resistance Rm. Also, by supplying current between the terminals C and D with the constant current circuit, a signal relating to temperature is generated based on a voltage between the terminals C and D.

Here, in the detecting device 100b of the second embodiment, the connecting portions 109a and 109b are formed on the lower insulating layer 103 that is bridge-supported or one-end-supported over the cavity portion 102a. Therefore, for example, in a case where the detecting device is controlled to let the heating element pattern 105 be heated so as to constantly keep a temperature of 300° C., a temperature of the heating element 105 can be more precisely controlled to become a desired temperature, where the resistance of the heating element 105 is controlled to become the same resistance as that of the reference resistor 211. As a consequence, a signal relating to the status of the atmosphere can be generated with very high precision.

In the following an example of a detecting circuit for operating the detecting device 100b will be described.

The detecting circuit of the second embodiment is similarly configured to the detecting circuit of the first embodiment, that is, replacing the detecting device 100a included in the detecting circuits shown in FIG. 4, FIG. 5 and FIG. 6 with the detecting device 100b.

Also, a sensor module of the second embodiment is similarly configured as the sensor module of the first embodiment, replacing the detecting device 100a included in the sensor module shown in FIG. 7 with the detecting device 100b.

Further, an image forming device of the second embodiment is similarly configured as the image forming device of the first embodiment, replacing the sensor module included in the image forming device of the first embodiment with the sensor module of the second embodiment.

As described above, according to the detecting device 100b, the detecting circuit, the sensor module and the image forming device of the second embodiment, the signal relating to temperature can be generated with high sensitivity. Also, the signal relating to the status of the atmosphere can be generated with high precision since a signal relating to the status of the atmosphere can be corrected based on the signal relating to temperature with high sensitivity. As a consequence, measures against noise, disposing an amplifier circuit with a large amplification factor in downstream of the detecting device 100b, and the like are not required.

Especially, in the second embodiment, a temperature of the heating element 105 can be more precisely controlled to become a desired temperature since the connecting portions 109a and 109b are formed on the lower insulating layer 103 that is bridge-supported or one-end-supported over the cavity portion 102a. As a consequence, a signal relating to the status of the atmosphere can be generated with very high precision.

Third Embodiment

In the following, an example of a detecting device 100c of a third embodiment will be described with reference to FIG. 10-FIG. 13. Additionally, in the third embodiment, an identical reference numeral will be applied to elements or the like that have substantially the same functions and configurations as those of in the first embodiment and the second embodiment, and descriptions thereof will be omitted.

Figure 10:
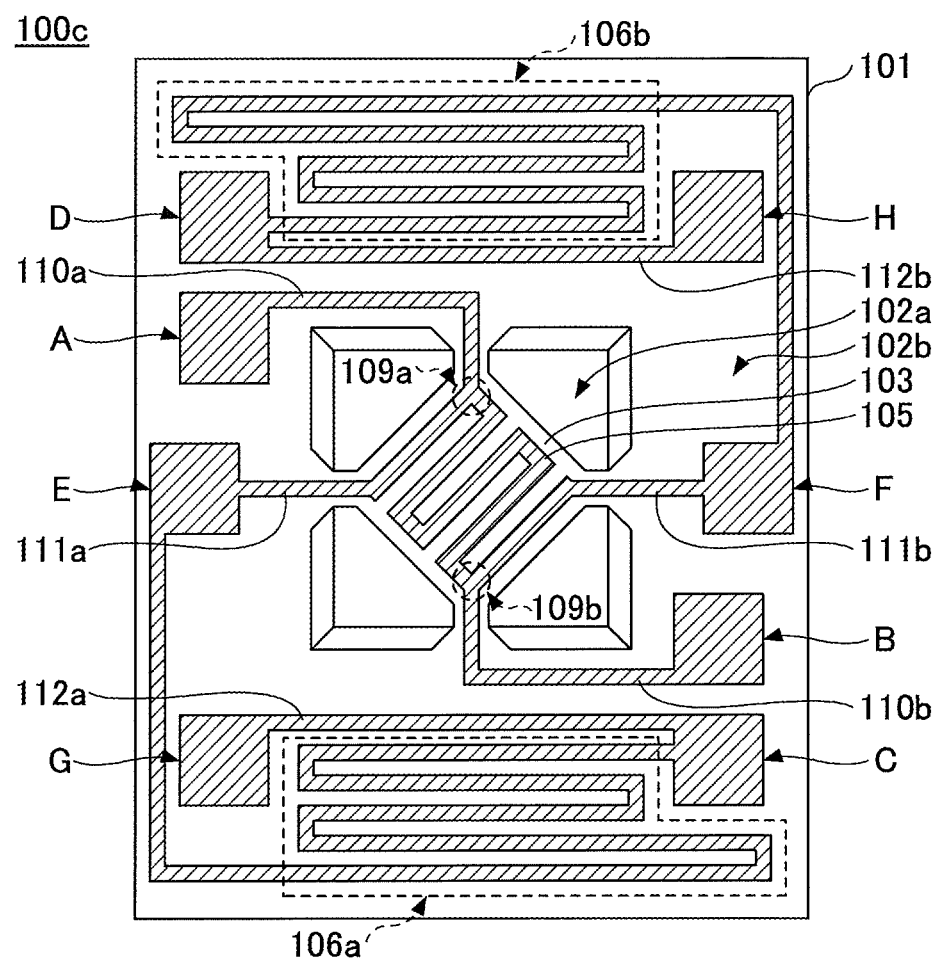
FIG. 10 is a schematic diagram of an example of the detecting device.

FIG. 10 is a schematic diagram of an example of the detecting device 100c. In FIG. 10, "A", "B", "C", "D", "E", "F", "G" and "H" respectively show the terminals for connecting with external circuits, for example.

Figure 11:
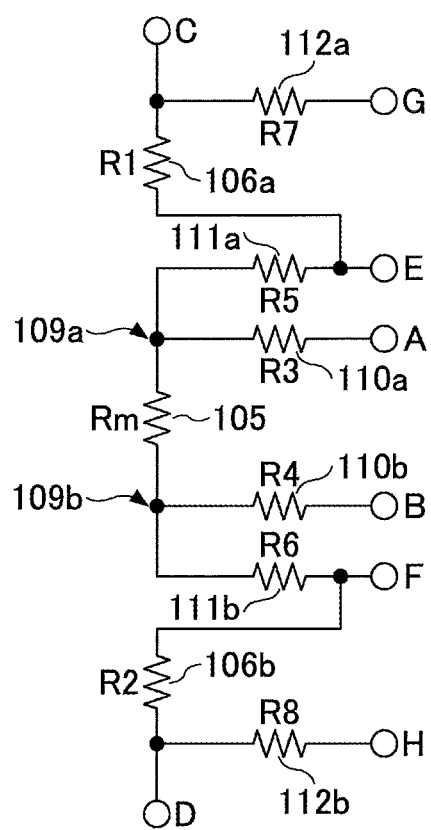
FIG. 11 is an equivalent circuit diagram of the detecting device shown in FIG. 10.

FIG. 11 is an equivalent circuit diagram of the detecting device 100c shown in FIG. 10. In FIG. 11, "Rm" shows a resistance of the heating element pattern 105, "R1" shows a resistance of the resistor pattern 106a, "R2" shows a resistance of the resistor pattern 106b, "R3" shows a parasitic resistance of a line 110a disposed between the connecting portion 109a and the terminal A, "R4" shows a parasitic resistance of a line 110b disposed between the connecting portion 109b and the terminal B, "R5" shows a parasitic resistance of a line 111a disposed between the connecting portion 109a and the terminal B, "R6" shows a parasitic resistance of a line 111b disposed between the connecting portion 109b and the terminal F, "R7" shows a parasitic resistance of a line 112a disposed between the terminal C and the terminal G, and "R8" shows a parasitic resistance of a line 112b disposed between the terminal D and the terminal H.

As described in FIG. 10 and FIG. 11, in the detecting device 100c of the third embodiment, where first ends of the resistor patterns 106a and 106b are respectively connected with the heating element pattern 105, the terminal C and the terminal G are formed at the other end of the resistor pattern 106a, and the terminal D and the terminal H are formed at the other end of the resistor pattern 106b, which is different from the second embodiment. In the third embodiment, a signal relating to temperature is generated by detecting a variance of voltage, indicative of a variance of the resistance of the heating element pattern 105 responsive to temperature, using the terminals C, D, G and H.

According to the detecting device 100c of the third embodiment, an effect of parasitic resistance caused by lines, etc., can be reduced since temperature is be detected using the plurality of the terminals C, D, G and H.

Figure 12:
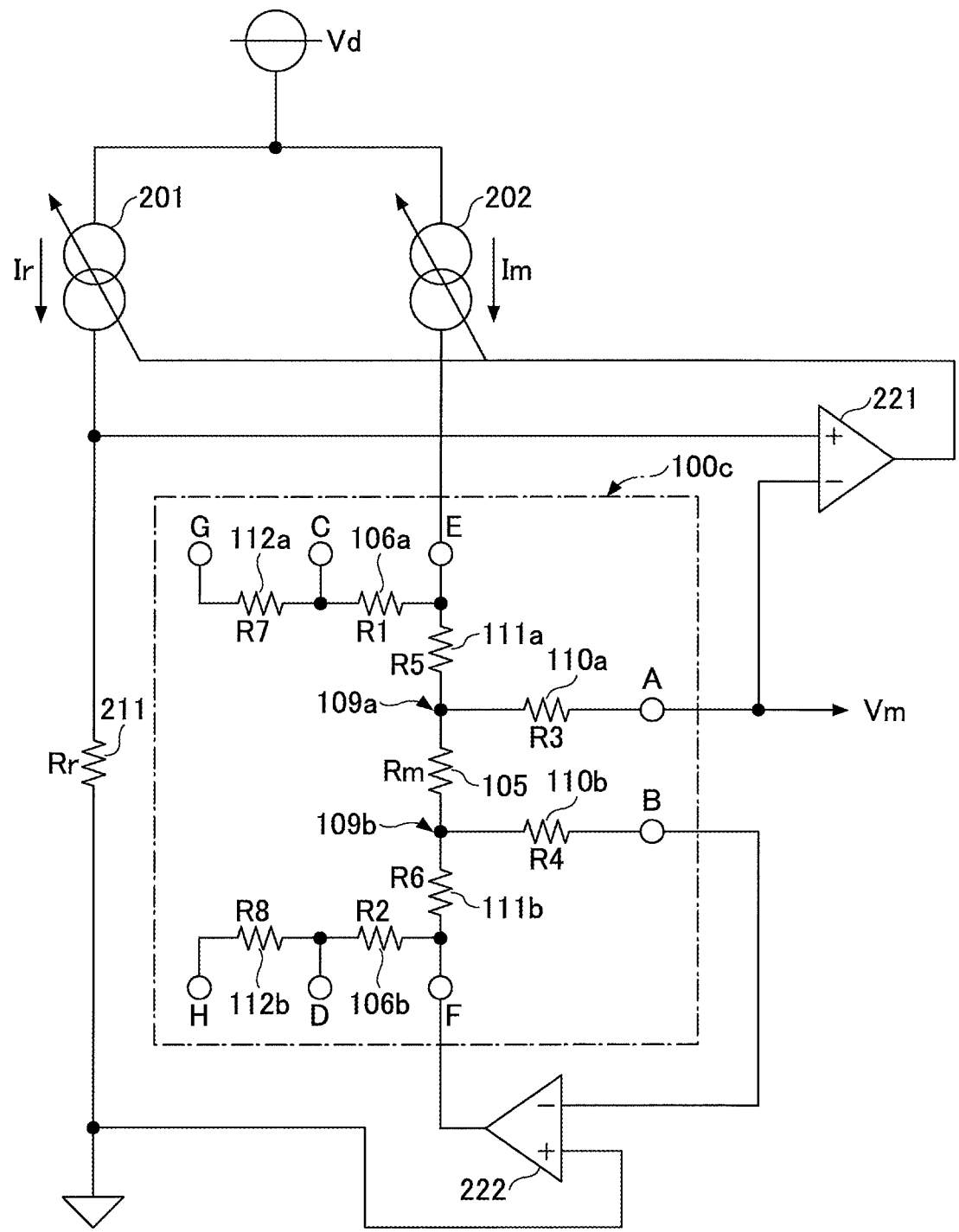
FIG. 12 is a circuit diagram of an example of a detecting circuit using the detecting device.

FIG. 12 is a circuit diagram of an example of a detecting circuit using the detecting device 100c.

As shown in FIG. 12, an output voltage Vm of the heating element pattern 105 indicates a difference between the voltages at both ends of the resistance Rm of the heating element 105. Therefore, the effect of a parasitic resistance R5 of the line 111a, a parasitic resistance R6 of the line 111b, a parasitic resistance (not shown) of a line disposed between the terminal E and the second constant current source 202, and a parasitic resistance (not shown) of a line disposed between the terminal F and a output terminal of the operational amplifier 222 can be eliminated.

Figure 13:
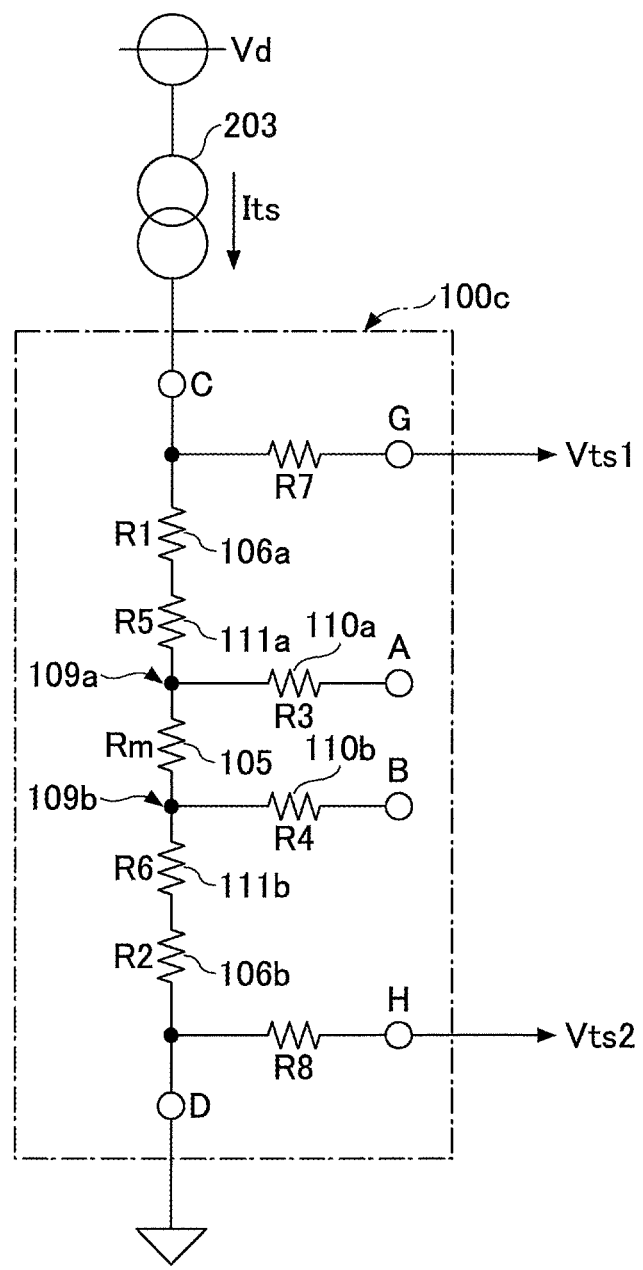
FIG. 13 is a circuit diagram of another example of the detecting circuit using the detecting device.

FIG. 13 is a circuit diagram of another example of the detecting circuit using the detecting device 100c.

As shown in FIG. 3, temperature in the vicinity of the resistor patterns 106a and 106b and the heating element pattern 105 is calculated by measuring a voltage Vts (=Vts1−Vts2) between the terminals G and H generated by current Its supplied from the third constant current source 203. Here, the voltage Vts is calculated by formula (3).

$$Vts = Its \times (R1 + R5 + Rm + R6 + R2) \quad (3)$$

Therefore, the effect of a parasitic resistance (not shown) of a line disposed between the third constant current source 203 and the terminal C and a parasitic resistance (not shown) of a line disposed between the terminal D and ground can be eliminated.

Also, a sensor module of the second embodiment is similarly configured to the sensor module of the first embodiment, replacing the detecting device 100a included in the sensor module shown in FIG. 7 with the detecting device 100c.

Further, an image forming device of the second embodiment is similarly configured to the image forming device of the first embodiment, replacing the sensor module included in the image forming device of the first embodiment with the sensor module of the third embodiment.

As described above, according to the detecting device 100c, the detecting circuit, the sensor module and the image forming device of the third embodiment, the signal relating to temperature can be generated with high sensitivity. Also, the signal relating to the status of the atmosphere can be generated with high precision since a signal relating to the status of the atmosphere can be corrected based on the signal relating to temperature with high sensitivity. As a consequence, measures against noise, disposing an amplifier circuit with a large amplification factor downstream of the detecting device 100c, and the like are not required.

Especially, in the third embodiment, the effect of parasitic resistance of lines, etc., can be reduced since a variance of voltage, indicative of a variance of the resistance of the heating element pattern responsive to temperature, using four terminals can be detected, where the heating element pattern is heated to around room temperature. As a consequence, a signal relating to temperature can be generated with very high precision.

Herein above, although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

The present application is based on Japanese Priority Application No. 2014-044848 filed on Mar. 7, 2014, the entire contents of which are hereby incorporated herein by reference.

What is claimed is:

1. A detecting device, comprising:
   a substrate having a cavity portion in the surface thereof;
   a thin-film layer formed over the cavity portion;
   an on-thin-film layer pattern formed on the thin-film layer;
   a first on-substrate pattern formed on the substrate;
   a second on-substrate pattern formed on the substrate;
   a first terminal formed with a first connecting portion to connect the on-thin-film layer and one end of the first on-substrate pattern;
   a second terminal formed with a second connecting portion to connect the on-thin-film layer and one end of the second on-substrate pattern;
   a third terminal formed on the other end of the first on-substrate pattern; and
   a fourth terminal formed on the other end of the second on-substrate pattern;
   wherein a resistance between the first connecting portion connecting the on-thin-film layer and said one end of the first on-substrate pattern and the second connecting portion connecting the on-thin-film layer and said one end of the second on-substrate pattern includes a resistance of the on-thin-film layer pattern, and
   a resistance between the third terminal formed on the other end of the first on-substrate pattern and the fourth terminal formed on the other end of the second on-substrate pattern includes the resistance of the on-thin-film layer pattern and a resistance of each of the first on-substrate pattern and the second on-substrate pattern, and the resistance of each of the first on-substrate pattern and the second on-substrate pattern is greater than the resistance of the on-thin-film layer pattern.

2. The detecting device as claimed in claim 1, wherein an area of connection between the on-thin-film layer pattern and the first on-substrate pattern is formed in the cavity portion, and an area of connection between the second on-thin-film layer pattern and the on-substrate pattern is formed in the cavity portion.

3. The detecting device as claimed in claim 2, further comprising a plurality of terminals formed at ends of the first on-substrate pattern and the second on-substrate pattern which are ends of the first on-substrate pattern and the second on-substrate pattern other than ends at the area of connection.

4. The detecting device as claimed in claim 1, further comprising a plurality of terminals formed at ends of the first on-substrate pattern and the second on-substrate pattern which are ends of the first on-substrate pattern and the second on-substrate pattern other than ends at the area of connection.

5. A detecting circuit, comprising:
the detecting device as claimed in claim 1;
a reference resistor;
a first constant current source, connected with the detecting device, configured to supply current to the detecting device;
a second constant current source, connected with the reference resistor, configured to be operated in combination with the first constant current source; wherein
the first constant current source and the second constant current source are controlled to respectively supply current to the detecting device and the reference resistor so that a voltage generated by the detecting device and a voltage generated by the reference resistor become equal.

6. A detecting circuit, comprising:
the detecting device as claimed in claim 2;
a reference resistor;
a first constant current source, connected with the detecting device, configured to supply current to the detecting device;
a second constant current source, connected with the reference resistor, configured to be operated in combination with the first constant current source; wherein
the first constant current source and the second constant current source are controlled to respectively supply current to the detecting device and the reference resistor so that a voltage generated by the detecting device and a voltage generated by the reference resistor become equal.

7. A detecting circuit, comprising:
the detecting device as claimed in claim 3;
a reference resistor;
a first constant current source, connected with the detecting device, configured to supply current to the detecting device;
a second constant current source, connected with the reference resistor, configured to be operated in combination with the first constant current source; wherein
the first constant current source and the second constant current source are controlled to respectively supply current to the detecting device and the reference resistor so that a voltage generated by the detecting device and a voltage generated by the reference resistor become equal.

8. A detecting circuit, comprising:
the detecting device as claimed in claim 4;
a reference resistor;
a first constant current source, connected with the detecting device, configured to supply current to the detecting device;
a second constant current source, connected with the reference resistor, configured to be operated in combination with the first constant current source; wherein
the first constant current source and the second constant current source are controlled to respectively supply current to the detecting device and the reference resistor so that a voltage generated by the detecting device and a voltage generated by the reference resistor become equal.

9. A detecting circuit, comprising:
a first circuit including the detecting device as claimed in claim 1, a reference resistor, a first constant current source connected with the detecting device and configured to supply current to the detecting device, and a second constant current source connected with the reference resistor and configured to be operated in combination with the first constant current source,
wherein the first circuit outputs a first output voltage generated by the detecting device, controlling the first constant current source and the second constant current source to respectively supply current to the detecting device and the reference resistor so that the first output voltage generated by the detecting device and a voltage generated by the reference resistor become equal;
a second circuit including the detecting device, and a third constant current source configured to supply current to the detecting device,
wherein the second circuit outputs a second output voltage generated by the detecting device by controlling the third constant current source to supply current to the detecting device; and
switching units disposed between the detecting device and the first constant current source, and between the detecting device and the third constant current source; wherein
the switching units switch to select the first circuit or the second circuit to output the first output voltage or the second output voltage generated by the detecting device as an output signal of the detecting circuit.

10. A detecting circuit, comprising:
a first circuit including the detecting device as claimed in claim 2, a reference resistor, a first constant current source connected with the detecting device and configured to supply current to the detecting device, and a second constant current source connected with the reference resistor and configured to be operated in combination with the first constant current source,
wherein the first circuit outputs a first output voltage generated by the detecting device, controlling the first constant current source and the second constant current source to respectively supply current to the detecting device and the reference resistor so that the first output voltage generated by the detecting device and a voltage generated by the reference resistor become equal;
a second circuit including the detecting device, and a third constant current source configured to supply current to the detecting device,
wherein the second circuit outputs a second output voltage generated by the detecting device by controlling the third constant current source to supply current to the detecting device; and switching units disposed between the detecting device and the first constant current source, and between the detecting device and the third constant current source; wherein the switching units switch to select the first circuit or the second circuit to output the first output voltage or the second output voltage generated by the detecting device as an output signal of the detecting circuit.

11. A detecting circuit, comprising:
a first circuit including the detecting device as claimed in claim 4, a reference resistor, a first constant current source connected with the detecting device and configured to supply current to the detecting device, and a second constant current source connected with the reference resistor and configured to be operated in combination with the first constant current source,
wherein the first circuit outputs a first output voltage generated by the detecting device, controlling the first constant current source and the second constant current source to respectively supply current to the detecting device and the reference resistor so that the first output voltage generated by the detecting device and a voltage generated by the reference resistor become equal;
a second circuit including the detecting device, and a third constant current source configured to supply current to the detecting device,
wherein the second circuit outputs a second output voltage generated by the detecting device by controlling the third constant current source to supply current to the detecting device; and
switching units disposed between the detecting device and the first constant current source, and between the detecting device and the third constant current source; wherein
the switching units switch to select the first circuit or the second circuit to output the first output voltage or the second output voltage generated by the detecting device as an output signal of the detecting circuit.

12. A sensor module, comprising:
a first circuit including the detecting device as claimed in claim 1, a reference resistor, a first constant current source connected with the detecting device and configured to supply current to the detecting device, and a second constant current source connected with the reference resistor and configured to be operated in combination with the first constant current source,
wherein the first circuit outputs a first output voltage generated by the detecting device as an output signal, controlling the first constant current source and the second constant current source to respectively supply current to the detecting device and the reference resistor so that the first output voltage generated by the detecting device and a voltage generated by the reference resistor become equal;
a second circuit including the detecting device, and a third constant current source configured to supply current to the detecting device,
wherein the second circuit outputs a second output voltage generated by the detecting device as an output signal by controlling the third constant current source to supply current to the detecting device; and
a control unit configured to process the first and second output voltages as output signals of the first circuit and the second circuit.

13. A image forming device, comprising a sensor module as claimed in claim 12.

14. A detecting circuit, comprising:
a first circuit including the detecting device as claimed in claim 3, a reference resistor, a first constant current source connected with the detecting device and configured to supply current to the detecting device, and a second constant current source connected with the reference resistor and configured to be operated in combination with the first constant current source,
wherein the first circuit outputs a first output voltage generated by the detecting device, controlling the first constant current source and the second constant current source to respectively supply current to the detecting device and the reference resistor so that the first output voltage generated by the detecting device and a voltage generated by the reference resistor become equal;
a second circuit including the detecting device, and a third constant current source configured to supply current to the detecting device,
wherein the second circuit outputs a second output voltage generated by the detecting device by controlling the third constant current source to supply current to the detecting device; and
switching units disposed between the detecting device and the first constant current source, and between the detecting device and the third constant current source; wherein
the switching units switch to select the first circuit or the second circuit to output the first output voltage or the second output voltage generated by the detecting device as an output signal of the detecting circuit.

15. A detecting circuit, comprising:
a current source configured to supply a current; and
a detecting device disposed to receive the current supplied by the current source, the detecting device including:
a substrate having a cavity portion in the surface thereof;
a thin-film layer formed over the cavity portion;
an on-thin-film layer pattern formed on the thin-film layer;
a first on-substrate pattern formed on the substrate;
a second on-substrate pattern formed on the substrate;
a first terminal formed with a first connecting portion to connect the on-thin-film layer and one end of the first on-substrate pattern;
a second terminal formed with a second connecting portion to connect the on-thin-film layer and one end of the second on-substrate pattern;
a third terminal formed on the other end of the first on-substrate pattern; and
a fourth terminal formed on the other end of the second on-substrate pattern;
wherein a resistance between the first connecting portion connecting the on-thin-film layer and said one end of the first on-substrate pattern and the second connecting portion connecting the on-thin-film layer and said one end of the second on-substrate pattern includes a resistance of the on-thin-film layer pattern,
a resistance between the third terminal formed on the other end of the first on-substrate pattern and the fourth terminal formed on the other end of the second on-substrate pattern includes the resistance of the on-thin-film layer pattern and a resistance of each of the first on-substrate pattern and the second on-substrate pattern, and the resistance of the first on-substrate pattern and the second on-substrate pattern is greater than the resistance of the on-thin-film layer pattern, and
the current supplied to the detecting device from the current source is supplied through the first terminal and then, at the first connecting portion connecting the on-thin-film layer and said one end of the first on-substrate pattern, is divided to (a) a first current path towards the third terminal and (b) a second current path towards (b1) the second connecting portion connecting the on-thin-film layer and said one end of the second on-substrate pattern, and (b2) the fourth terminal formed on the other end of the second on-substrate pattern.

\* \* \* \* \*